(12) United States Patent
Liu et al.

(10) Patent No.: US 10,207,259 B2
(45) Date of Patent: Feb. 19, 2019

(54) HYBRID SAPO-34/ZSM-5 CATALYST, ITS PREPARATION AND ITS USE

(71) Applicant: Dow Global Technologies LLC, Midland, MI (US)

(72) Inventors: Yu Liu, Freeport, TX (US); Andrzej Malek, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/501,873

(22) PCT Filed: Sep. 9, 2015

(86) PCT No.: PCT/US2015/049068
§ 371 (c)(1),
(2) Date: Feb. 6, 2017

(87) PCT Pub. No.: WO2016/044010
PCT Pub. Date: Mar. 24, 2016

(65) Prior Publication Data
US 2018/0178204 A1 Jun. 28, 2018

Related U.S. Application Data

(60) Provisional application No. 62/052,533, filed on Sep. 19, 2014.

(51) Int. Cl.

| | |
|---|---|
| *B01J 29/06* | (2006.01) |
| *B01J 29/80* | (2006.01) |
| *B01J 29/00* | (2006.01) |
| *C01B 39/02* | (2006.01) |
| *B01J 35/00* | (2006.01) |
| *B01J 37/03* | (2006.01) |
| *C01B 39/04* | (2006.01) |
| *C01B 39/40* | (2006.01) |
| *B01J 29/40* | (2006.01) |
| *B01J 29/85* | (2006.01) |
| *C01B 39/54* | (2006.01) |
| *C07C 1/20* | (2006.01) |
| *B01J 37/04* | (2006.01) |
| *B01J 37/08* | (2006.01) |
| *B01J 37/10* | (2006.01) |

(52) U.S. Cl.
CPC .............. *B01J 29/80* (2013.01); *B01J 29/005* (2013.01); *B01J 29/06* (2013.01); *B01J 29/40* (2013.01); *B01J 29/85* (2013.01); *B01J 35/0006* (2013.01); *B01J 37/031* (2013.01); *B01J 37/04* (2013.01); *B01J 37/08* (2013.01); *B01J 37/10* (2013.01); *C01B 39/023* (2013.01); *C01B 39/04* (2013.01); *C01B 39/40* (2013.01); *C01B 39/54* (2013.01); *C07C 1/20* (2013.01); *B01J 2029/062* (2013.01); *B01J 2229/10* (2013.01); *B01J 2229/30* (2013.01); *B01J 2229/40* (2013.01); *B01J 2229/62* (2013.01); *C07C 2529/40* (2013.01); *C07C 2529/85* (2013.01); *Y02P 20/52* (2015.11); *Y02P 30/42* (2015.11)

(58) Field of Classification Search
CPC ........ B01J 29/005; B01J 29/06; B01J 29/062; B01J 29/40; B01J 29/85; B01J 2229/10; B01J 2229/30; B01J 2229/40; B01J 35/0006; B01J 37/031; B01J 2029/062; C01B 39/023; C01B 39/04; C01B 39/40; C01B 39/54
USPC ........ 502/60, 63, 64, 77, 214; 423/700, 701, 423/709, 716
See application file for complete search history.

(56) References Cited

U.S. PATENT DOCUMENTS

| | | |
|---|---|---|
| 3,702,886 A | 11/1972 | Argauer et al. |
| 4,499,327 A | 2/1985 | Kaiser |
| 4,582,815 A | 4/1986 | Bowes |
| 5,053,374 A | 10/1991 | Absil et al. |
| 5,182,242 A | 1/1993 | Marler |
| 7,230,151 B2 | 6/2007 | Martens et al. |
| 2006/0106270 A1* | 5/2006 | Glover ...................... C07C 1/20 585/639 |
| 2008/0106270 A1 | 5/2008 | Crick |
| 2008/0242910 A1 | 10/2008 | Kaines et al. |

OTHER PUBLICATIONS

H.J.Chae et al: "Physicochemical characteristics of ZSM-5/SAPO-34 composite catalyst for MTO reaction", J. Phys. Chem. Solid 71 (2010)600.
Razavian Marjan et al, Synethesis and application of ZSM-5/SAPO-34 and SAPO-45/ZSM-5 composite systems for propylene yield enhancement in propane dehydrogenation process:, Microporous and Mesoporous Materials, Elsevier Science Publishing, New York, US, vol. 201, Sep. 16, 2014 (Sep. 16, 2014), pp. 176-189.
Chao Duan et al: "Hyrrotherrnally Synthesized HZSM-5/SAPO-34 Composite Zeolite Catalyst for Ethanol Conversion to Propylene", Catalysis Letters, Kluwer Academic Publishers-Plenum Publishers, NE, vol. 141, No. 12, Oct. 27, 2011 (Oct. 27, 2011), pates 1821-1827.

(Continued)

*Primary Examiner* — Elizabeth D Wood

(57) ABSTRACT

Prepare a hybrid SAPO-34/ZSM-5 catalyst via sequential steps as follows: a) form a mixture consisting essentially of ZSM-5 as a sole source of silicon atoms, aluminum isopropoxide and a solution of orthophosphoric acid; b) combine the mixture with an aqueous solution of tetraethylammonium hydroxide to form a reaction mixture; and c) subject the reaction mixture to hydrothermal conditions for a period of time sufficient to convert the reaction mixture to a hybrid SAPO-34/ZSM-5 catalyst. Use the hybrid catalyst in converting an oxygenate (methanol and/or dimethyl ether) to an olefin.

3 Claims, No Drawings

(56) References Cited

OTHER PUBLICATIONS

Zheng Jiajun et al: "Hierarchiai core-shell zeolite composite ZSM-5@SAPO-34 fabricated by using ZSM-5 as the nutrients for the growth of SAPO-34", Microporous and Mesoporous Materials vol. 206, Dec. 16, 2014 (Dec. 16, 2014), pp. 114-120.
PCT/US2015/049068, International Search Report dated Mar. 24, 2016.
PCT/US2015/049068, International Preliminary Report on Patentability dated Mar. 21, 2017.
PCT/US2015/049068, Written Opinion of the International Searching Authority dated Mar. 24, 2016.

\* cited by examiner

HYBRID SAPO-34/ZSM-5 CATALYST, ITS PREPARATION AND ITS USE

The present application claims the benefit of U.S. Provisional Application No. 62/052,533, filed on Sep. 19, 2014.

This invention relates generally to a hybrid SAPO-34/ZSM-5 catalyst and specifically to such a catalyst prepared in-situ growth of SAPO-34 over ZSM-5. This invention also relates to use of the hybrid catalyst in converting an alcohol to an olefin, specifically converting methanol to an olefin.

Ho-Jeong Chae et al., in "Physicochemical characteristics of ZSM-5/SAPO-34 composite catalyst for MTO reaction", *Journal of Physics and Chemistry of Solids* 71 (2010), pages 600-603, presents teachings related to the title catalysts and their hydrothermal synthesis in an autoclave. A first hydrothermal synthesis technique involves successive crystallization of SAPO-34 synthetic gel after ZSM-5 crystallization. A second hydrothermal synthesis technique is a one step crystallization of SAPO-34 synthetic gel using commercial ZSM-5 powder as a seed. In the first technique, one synthesizes and then crystallizes ZSM-5 to form a ZSM-5 slurry and then admixes the slurry with components of SAPO-34 gel, including a silica source (fumed silica), forms SAPO-34 gel and then crystallizes the SAPO-34. The teachings include a comparison of composite catalysts prepared by the two techniques with ZSM-5 alone, SAPO-34 alone and a physical mixture of ZSM-5 and SAPO-34.

United States Patent Application Publication (USPAP) 2006/0106270 (Glover et al.) discloses use of a dual-function catalyst for conversion of an oxygenate to propylene. The catalyst contains a zeolitic molecular sieve having a structure corresponding to ZSM-5 or ZSM-11 or an ELAPO molecular sieve having a structure corresponding to SAPO-34 or a mixture of these materials. "Oxygenates" include aliphatic alcohols, ethers, carbonyl compounds (e.g. aldehydes, ketones and carboxylic acids) and mixtures of these materials. When EL is silicon, preferred sources include fumed, colloidal or precipitated silica. Preparation of a mixture of zeolitic (e.g. ZSM-5) and non-zeolitic (e.g. SAPO-34) catalysts involves physically mixing particles containing zeolitic material with particles containing the non-zeolitic material as well as mixing the two types of material into a phosphorous-modified aluminum matrix to form particles having both types of material present therein.

U.S. Pat. No. 4,499,327 (Kaiser) teaches use of silicoaluminophosphate (SAPO) molecular sieve catalysts in converting a feedstock such as methanol, ethanol, dimethyl ether, diethyl ether or a mixture thereof to a light ($C_2$, $C_3$ and/or $C_4$) olefin. SAPO molecular sieves comprise a molecular framework of $[AlO_2]$, $[PO_2]$ and $[SiO_2]$ tetrahedral units.

U.S. Pat. No. 7,230,151 (Martens et al.) discloses as process for making an olefin, especially ethylene and propylene, from an oxygenate feed using two or more zeolite catalysts. One of the catalysts may be ZSM-5 and the other may be a 10-ring molecular sieve such as ZSM-22, ZSM-23, ZSM-35, ZSM-48 and mixtures thereof.

U.S. Pat. No. 3,702,886 (Argauer) describes ZSM-5 and its preparation. See also U.S. Pat. No. 4,582,815, U.S. Pat. No. 5,053,374 and U.S. Pat. No. 5,182,242. ZSM-5 is a family of crystalline zeolites with MFT framework structure according to IZA (International Zeolite Association) and with composition that can be expressed as $M_{n/m}[Al_nSi_{96-n}O_{192}]\sim 16H_2O$ where n<27 and M is a cation and m is the valence of said cation. ZSM-5 synthesis may involve preparing a solution containing tetrapropyl ammonium hydroxide, sodium oxide, an oxide of aluminum, an oxide of silica and water, subjecting the solution to reaction conditions consisting of a temperature of from 100° C. to 175° C. for a time at temperature of from 6 hours to 60 days.

In some aspects, this invention is a process for preparing a hybrid SAPO-34/ZSM-5 catalyst that comprises sequential steps as follows: a) forming a mixture consisting essentially of ZSM-5 as a sole source of silicon atoms, aluminum isopropoxide and a solution of orthophosphoric acid; b) combining the mixture with an aqueous solution of tetraethylammonium hydroxide to form a reaction mixture; and c) subjecting the reaction mixture to hydrothermal conditions for a period of time sufficient to convert the reaction mixture to a hybrid SAPO-34/ZSM-5 catalyst, the hydrothermal conditions comprising a temperature within a range of from 190 degrees centigrade (° C.) to 210° C., preferably 200° C. plus or minus 5° C., and autogenous pressure.

In some aspects, the process further comprises a sequential step d) that follows step c) wherein the hybrid SAPO-34/ZSM-5 catalyst undergoes calcination in an oxygen-containing atmosphere at a temperature within a range of from 550° C. to 650° C. for a period of time within a range of from one hour to 12 hours.

In some aspects, this invention is a process for converting an oxygenate that comprises methanol and dimethyl ether and, optionally ethanol, to at least one olefin comprising placing the oxygenate in operative contact with the above hybrid SAPO-34/ZSM-5 catalyst.

In some aspects, ZSM-5 is present in the catalyst in a weight ratio of SAPO-34 to ZSM-5 that is greater than 50:50, preferably within a range of from 96:4 to 85:15, and more preferably within a range of from 94:6 to 90:10.

The hybrid catalyst has utility in converting an oxygenate (e.g. methanol, ethanol and/or dimethyl ether) to an olefin, preferably at least one of ethylene, propylene and butenes, specifically in a conversion that has an improved lifetime with higher $C_2/C_3$ olefin ratio while maintaining at least the same overall selectivity to $C_2$ to $C_4$ olefins compared to a physical mixture of SAPO-34 and ZSM-5 at the same ratio of SAPO-34 to ZSM-5.

COMPARATIVE EXAMPLE (CEX A)—PHYSICAL MIXTURE

Physically mix 1.5 grams (g) fresh calcined SAPO-34 with 1.5 g calcined ZSM-5 (Si/Al2=280) in mortar and pestle. Subject the resulting catalyst to catalyst testing as provided below and summarize results in Table 1 below.

CEx B—Physical Mixture

Physically mix 1.5 grams (g) fresh calcined SAPO-34 with 0.17 g calcined ZSM-5 (Si/Al2=280) in mortar and pestle. Subject the resulting catalyst to catalyst testing as provided below and summarize results in Table 1 below.

CEx C—Physical Mixture

Physically mix 1.5 grams (g) fresh calcined SAPO-34 with 0.1 g calcined ZSM-5 (Si/Al2=280) in mortar and pestle. Subject the resulting catalyst to catalyst testing as provided below and summarize results in Table 1 below.

CEx D—Hybrid

With stirring, combine 8.2 g of aluminum isopropoxide $(Al(OC_3H_7)_3)$ with a solution of 4.6 g of 85 wt. % orthophosphoric acid in 8.4 g of water to form a preliminary mixture. Add 3 g of unclacined ZSM-5 (NH4 form, $SiO_2$/Al2O3=280) to the preliminary mixture and continue stirring for 30 minutes (min). With continued stirring, add 16.8 g of an aqueous solution of 35 wt % tetraethylammonium hydroxide (TEAOH) to form a reaction mixture. Place the reaction mixture in a stainless steel pressure vessel lined with polytetrafluoroethylene and place the vessel and its contents in an oven operating at a set point temperature of 200° C. at autogeneous pressure for 120 hours (hr). Recover a solid catalytic reaction product from the vessel contents by centrifugation. Wash the catalytic reaction product with water, then dry it in air at 100.° C. Subject the catalytic reaction product to catalyst testing as provided below and summarize results in Table 1 below.

EXAMPLE (EX) 1—HYBRID

Replicate CEx D, but change the amount of uncalcined ZSM-5 to 1 g. Summarize results in Table 1 below.

EX 2—HYBRID

Replicate CEx D, but change the amount of uncalcined ZSM-5 to 0.8 g. Summarize results in Table 1 below.

TABLE 1

| Ex/CEx | | A | B | C | D | 1 | 2 |
|---|---|---|---|---|---|---|---|
| SAPO-34:ZSM-5 ratio (w/w) | | 50:50 | 90:10 | 94:6 | 50:50 | 90:10 | 94:6 |
| Cycle time (g of MeOH/g of catalyst | | >48 | 5.9 | 9.0 | >48 | 15.3 | 26.0 |
| Selectivity % @ 3.5 g MeOH/g of catalyst | Ethylene | 14.9 | 36.6 | 29.9 | 13.6 | 38.1 | 34.9 |
| | Propylene | 42.9 | 38.5 | 36.2 | 27.7 | 34.7 | 35.9 |
| | Ethylene/Propylene ratio | 0.3 | 0.9 | 0.8 | 0.5 | 1.1 | 1.0 |
| | Butenes | 19.1 | 16.9 | 16.1 | 11.6 | 19.0 | 20.0 |
| | Ethylene through Butenes (%) | 76.9 | 92.0 | 82.2 | 52.9 | 91.8 | 90.8 |
| | Methane through butane (%) | 9.7 | 0.9 | 2.1 | 17.1 | 1.2 | 1.5 |
| | Pentane plus Hexane | 8.2 | 6.6 | 11.2 | 11.7 | 5.7 | 6.0 |
| | Aromatics | 5.2 | 0.3 | 2.5 | 18.1 | 1.2 | 1.6 |

Catalyst Testing

Evaluate catalyst performance in a continuous flow micro reactor system (stainless steel tube (¼ inch by 6 inches (6.35 millimers (mm) by 15.24 centimeters (cm)) with 200 grams (g) of 20 mesh to 50 mesh (295 micrometers (um) to 853 um) catalyst sandwiched between two aliquots (2.5 inches (6.4 cm)) of 20 mesh to 50 mesh quartz chips at ambient pressure (nominally one atmosphere (101.32 kilopascals (KPa)). Before initiating feed of methanol, heat treat the catalyst at a temperature of 500° C. for two hours (hr) to remove adsorbed water and volatile organic materials from the catalyst in helium (20 ml/min flow rate). After the heat treatment, feed methanol into the reactor system at a rate of 6 microliters per minute (ul/min) using an ISCO pump (100 DM) together with a mixed gas of He and $N_2$ (5 vol %) of 20 ml/min at standard temperature and pressure (STP) (nominally one atmosphere (101.32 kilopascals (KPa) and 25° C.)).

The data presented in Table 1 demonstrate that the hybrid catalyst of Ex 1 and Ex 2 shows an improved lifetime with higher $C_2/C_3$ olefin ratio while maintaining at least the same overall selectivity to $C_2$ to $C_4$ olefins compared to a physical mixture of SAPO-34 and ZSM-5 at the same ratio of SAPO-34 to ZSM-5 (CEx B and C).

What is claimed is:

1. A process for preparing a hybrid SAPO-34/ZSM-5 catalyst that comprises sequential steps as follows: a) forming a mixture consisting essentially of ZSM-5 as a sole source of silicon atoms, aluminum isopropoxide and a solution of orthophosphoric acid; b) combining the mixture with an aqueous solution of tetraethylammonium hydroxide to form a reaction mixture; and c) subjecting the reaction mixture to hydrothermal conditions for a period of time sufficient to convert the reaction mixture to a hybrid SAPO-34/ZSM-5 catalyst, the hydrothermal conditions comprising a temperature within a range of from 190 degrees centigrade (° C.) to 210° C. and autogenous pressure, wherein ZSM-5 is present in a weight ratio of SAPO-34 to ZSM-5 within a range of from 96:4 to 85:15.

2. The process of claim 1, wherein ZSM-5 is present in a weight ratio of SAPO-34 to ZSM-5 within a range of from 94:6 to 90:10.

3. The process of claim 1, further comprising a sequential step d) that follows step c) wherein the hybrid SAPO-34/ZSM-5 catalyst undergoes calcination in an oxygen-containing atmosphere at a temperature within a range of from 550° C. to 650° C. for a period of time within a range of from one hour to 12 hours.

* * * * *